United States Patent
Hogendoorn et al.

(10) Patent No.: US 10,234,314 B2
(45) Date of Patent: Mar. 19, 2019

(54) NUCLEAR MAGNETIC FLOWMETER AND METHOD FOR OPERATING NUCLEAR MAGNETIC FLOWMETERS

(71) Applicant: Krohne AG, Basel (CH)

(72) Inventors: Cornelis Johannes Hogendoorn, Spijk (NL); Rutger Reinout Tromp, Dordrecht (NL); Marco Leendert Zoeteweij, Endrik-Ido-Ambach (NL); John Justin Freeman, Brookshire, TX (US); Matthias Appel, Houston, TX (US)

(73) Assignee: KROHNE AG, Basel (CH)

( * ) Notice: Subject to any disclaimer, the term of this patent is extended or adjusted under 35 U.S.C. 154(b) by 436 days.

(21) Appl. No.: 14/913,055

(22) PCT Filed: Aug. 11, 2014

(86) PCT No.: PCT/EP2014/002204
§ 371 (c)(1),
(2) Date: Feb. 19, 2016

(87) PCT Pub. No.: WO2015/024636
PCT Pub. Date: Feb. 26, 2015

(65) Prior Publication Data
US 2016/0202100 A1    Jul. 14, 2016

(30) Foreign Application Priority Data

Aug. 21, 2013  (DE) .......................... 10 2013 013 745
Feb. 24, 2014  (DE) .......................... 10 2014 002 392

(51) Int. Cl.
*G01F 1/58*    (2006.01)
*G01F 1/74*    (2006.01)
(Continued)

(52) U.S. Cl.
CPC ............. *G01F 1/716* (2013.01); *G01F 1/56* (2013.01); *G01F 1/58* (2013.01); *G01F 1/74* (2013.01);
(Continued)

(58) Field of Classification Search
CPC ... G01F 1/716; G01F 1/56; G01F 1/58; G01F 1/74; G01N 24/08; G01N 24/081;
(Continued)

(56) References Cited

U.S. PATENT DOCUMENTS 4,613,818 A    9/1986 Battocletti et al.
4,638,251 A    1/1987 King
(Continued)

FOREIGN PATENT DOCUMENTS

SU              819657 A1    4/1981

*Primary Examiner* — Susan S Lee
(74) *Attorney, Agent, or Firm* — David S. Safran; Roberts Mlotkowski Safran Cole & Calderon, P.C.

(57) ABSTRACT

A nuclear magnetic flowmeter (1) for determining the flow of a medium flowing through a measuring tube (2) having a magnetic field generator (4), a measuring unit (5) and an antennae unit (6) with an antenna (7). wherein the antennae unit (6) has at least one further antenna (11, 12), that is designed as a coil and is designed for transmitting the excitation signal to the magnetized medium (3) and for detecting the measuring signal over a further measuring section (13, 14) aligned parallel to the longitudinal axis (8) of the measuring tube and located in the magnetic field path (9), and the measuring section (10) and the further measuring section (13, 14) are different.

19 Claims, 3 Drawing Sheets

(51) Int. Cl.
| | |
|---|---|
| *G01F 1/716* | (2006.01) |
| *G01N 24/08* | (2006.01) |
| *G01R 33/34* | (2006.01) |
| *G01R 33/44* | (2006.01) |
| *G01R 33/563* | (2006.01) |
| *G01F 1/56* | (2006.01) |

(52) U.S. Cl.
CPC ........... *G01N 24/08* (2013.01); *G01N 24/081* (2013.01); *G01N 24/082* (2013.01); *G01N 24/085* (2013.01); *G01R 33/34* (2013.01); *G01R 33/34053* (2013.01); *G01R 33/34061* (2013.01); *G01R 33/56308* (2013.01); *G01R 33/448* (2013.01)

(58) Field of Classification Search
CPC .... G01N 24/082; G01N 24/085; G01R 33/34; G01R 33/34053; G01R 33/34061; G01R 33/56308; G01R 33/448
USPC ........................................................ 324/309
See application file for complete search history.

(56) References Cited

U.S. PATENT DOCUMENTS

| | | |
|---|---|---|
| 7,872,474 B2 | 1/2011 | Pusiol et al. |
| 9,835,484 B2 * | 12/2017 | Hogendoorn ............. G01F 1/58 |
| 2012/0092007 A1 | 4/2012 | Li et al. |

* cited by examiner

NUCLEAR MAGNETIC FLOWMETER AND METHOD FOR OPERATING NUCLEAR MAGNETIC FLOWMETERS

BACKGROUND OF THE INVENTION

Field of the Invention

The invention relates to a nuclear magnetic flowmeter for determining the flow of a medium flowing through a measuring tube having a magnetic field generator, a measuring unit and an antennae unit with an antenna, wherein the magnetic field generator permeates the flowing medium with a magnetic field having at least a component perpendicular to a longitudinal axis of the measuring tube over a magnetic field path aligned parallel to the longitudinal axis of the measuring tube for magnetizing the medium, wherein the measuring unit is designed to generate excitation signals exciting the magnetized medium and to measure the measuring signals caused by the excitation signals in the magnetized medium and wherein the antenna is designed as a coil and is designed for transmitting the excitation signals to the magnetized medium and for detecting the measuring signal over a measuring section aligned parallel to the longitudinal axis of the measuring tube and located in the magnetic field path. Furthermore, the invention relates to a method for operating nuclear magnetic flowmeters.

Description of Related Art

The atomic nuclei of the elements having nuclear spin also have a magnetic moment $\mu$ caused by nuclear spin. Nuclear spin can be regarded as angular momentum describable by a vector, and accordingly, the magnetic moment can also be described by a vector that is aligned parallel to the vector of the angular momentum. The vector of the magnetic moment of an atomic nucleus, in the presence of a macroscopic magnetic field, aligns itself parallel to the vector of the macroscopic magnetic field at the location of the atomic nucleus. The vector of the magnetic moment of the atomic nucleus precesses around the vector of the macroscopic magnetic field at the location of the atomic nucleus. The frequency of precession is the Larmor frequency and is the product of the gyromagnetic ratio and the value of the magnetic flux density at the location of the atomic nucleus. Therefore, the Larmor frequency is proportional to the value of the magnetic flux density at the location of the atomic nucleus. The gyromagnetic ratio is at a maximum for hydrogen nuclei.

In the absence of a macroscopic magnetic field due to the statistical uniform distribution of the individual magnetic moments of the atomic nuclei, a plurality of K atomic nuclei in a volume V that does have a magnetic moment do not have macroscopic magnetization. The presence of a macroscopic magnetic field disturbs the statistical uniform distribution of the alignment of the individual magnetic moments of the atomic nuclei, and a macroscopic magnetic magnetization builds up parallel to the macroscopic magnetic field. The time course of the process of aligning the magnetic moment in the macroscopic magnetic field is characterized by the spin-lattice-relaxation time constant $T_1$ and has an exponentially declining course. The value of the spin-lattice-relaxation time constant is, in turn, characteristic for different substances.

Nuclear magnetic flowmeters of the type described in the introduction are designed for determining the flow of the medium flowing through the measuring tube. The medium can contain one or more phases. In a single-phase medium, the determination of the flow is conducted by determining the flow velocity of the medium in a measuring tube. The determination of the flow of a multi-phase medium includes, in addition to determining the flow velocity of each of the phases, also determining the portion of each phase in the medium. Each phase of the medium must thereby have atomic nuclei with a magnetic moment, so that the phases are magnetizable in a magnetic field. If the phases of the medium have different spin-lattice-relaxation constants, then their portion of the medium can be determined. Multi-phase medium extracted from oil sources consist essentially of the two fluid phases crude oil and saltwater and the gaseous phase natural gas, wherein all phases contain hydrogen nuclei and have different spin-lattice-relaxation time constants. Thus, nuclear magnetic flowmeters of the type described in the introduction are suitable, in particular, for measuring the flow of multi-phase mediums extracted from oil sources.

Measuring methods for determining the portion of the individual phases in the medium provide that the magnetization of the medium is determined after differing exposure durations of the magnetic field generated by the magnetic field generator on the medium. The determination of the magnetization of the medium after a certain exposure duration of the magnetic field is conducted with the measuring unit by exciting the magnetized medium with excitation signals, measuring the measuring signals caused by the excitation signals in the magnetized medium and evaluating the measuring signals. The precessing vectors of the magnetic moments of the individual atomic nuclei, uncorrelated before excitation of the medium are correlated by the excitation, which initially means fixed relationships between the precessing vectors of the magnetic moments. As time lapses after excitation, the correlation subsides exponentially due to different mechanisms, this is called dephasing and is characterized by the relaxation time constant $T_2$ here. The value of the relaxation time constant $T_2$ is characteristic for different substances. Accordingly, the measuring signals have a harmonic oscillation, which is characterized by the angular Larmor frequency and an exponentially declining amplitude. The measuring unit further determines the portions of the individual phases in the medium from differing exposure durations of the magnetic field on the medium and, thereby, certain magnetizations. The coil-like antenna of the antennae unit thereby transmits, on the one hand, the excitation signals to the medium and detects, on the other hand, the measuring signals of the excited medium. The antennae unit transmits the excitation signals from the measuring unit to the antenna and transmits the measuring signals from the antenna to the measuring unit.

Nuclear magnetic flowmeters of the type described in the introduction and known from the prior art vary the effective exposure duration of the magnetic field on the medium by changing the magnetic field, wherein the change of the magnetic field is caused by a mechanism.

A nuclear magnetic flowmeter of the type described in the introduction is known from U.S. Pat. No. 7,872,474 B2. The magnetic field generator is comprised of several magnet arrangements arranged successively around the measuring tube along the longitudinal axis of the measuring tube. Each of the magnet arrangements is rotatable around the longitudinal axis of the measuring tube and permeates the medium flowing in the measuring tube with a magnetic field having a direction. The directions of the individual magnetic fields of the magnet arrangements can thereby be aligned parallel or anti-parallel to one another. If, for example, the magnetic field generator comprises four magnet arrangements and if the directions of the magnetic fields of the four magnet arrangements are aligned parallel, then the effective exposure duration of the magnetic field on the medium is at a maximum. If the direction of the magnetic field of one of the magnet arrangements is anti-parallel to the directions of the magnetic fields of the remaining three magnet arrangements, then the effective exposure duration is only half as long as before. One of the three magnet arrangements, whose magnetic field directions are aligned parallel, compensates the magnetization of the medium using the magnet arrangement, whose direction of the magnetic field is aligned anti-parallel. Rotation of the individual magnet arrangements requires an appropriate mechanism. This mechanism, like any mechanism, is associated with costs, requires space, requires maintenance and, despite maintenance, is only reliable within certain limits.

SUMMARY OF THE INVENTION

An object of aspects of the invention is to provide a nuclear magnetic flowmeter having an improved reliability and to provide a method for operating nuclear magnetic flowmeters.

The nuclear magnetic flowmeter according to the invention, in which the above derived and described object is achieved, is characterized in that the antennae unit has at least one further antenna, that the further antenna is designed as a coil and is designed for transmitting the excitation signals to the magnetized medium and for detecting the measuring signals over a further measuring section aligned parallel to the longitudinal axis of the measuring tube and located in the magnetic field path, and that the measuring section and the further measuring section are different.

The antennae unit comprises at least two antennae, wherein each of the antennae is designed as a coil and is designed for transmitting the excitation signals to the magnetized medium and for detecting the measuring signals over a measuring section located in the magnetic field path and aligned parallel to the longitudinal axis of the measuring tube. Each of measuring sections is clearly defined by its length parallel to the longitudinal axis of the measuring tube and its location on the longitudinal axis of the measuring tube. At least two of the measuring sections can be located either successively or overlapping in the magnetic field path.

Due to the different measuring sections of the antennae, the excitation of the medium with the excitation signals and then the detection of the measuring signals of the medium caused by the excitation signals is conducted after different exposure durations of the magnetic field on the medium. The exposure duration of the magnetic field on the medium results directly from the distance in the direction of flow of the medium from the beginning of the magnetic field path to the respective antenna and the flow velocity of the medium in the measuring tube.

The nuclear magnetic flowmeter according to the invention has, as opposed to nuclear magnetic flowmeters of the type described in the introduction and known from the prior art, the advantage that the mechanism for variation of the effective exposure duration of the magnetic field on the medium is omitted. Due to the omission of the mechanism, the construction of the nuclear magnetic flowmeter according to the invention is substantially simplified. Maintenance efforts and maintenance costs sink thereby and the reliability of the nuclear magnetic flowmeter according to the invention is increased. In comparison to the mechanism, coil-like antennae are substantially less expensive, which is why a greater number of antennae can be implemented for the same costs. The greater number of antennae make the measurement of the magnetization of the medium possible at a greater number of different exposure durations of the magnetic field on the medium, which improves measurement reliability.

In a preferred design of the nuclear magnetic flowmeter according to the invention, it is provided that the winding densities of at least two of the coil-like antennae are the same. Same winding densities simplify the production of the coil-like antennae, which makes them less costly. Furthermore, the coil-like antennae having the same winding densities have similar electric properties, which simplifies the tuning of the measuring units.

It has been seen that a length of the measuring section proportional to the flow velocity of the medium delivers better measurement results than a measuring section having a constant length for the entire flow velocity range of the medium. If, for example, the flow velocity is determined in that the flowing medium is excited over a measuring section and then the flow velocity is determined from the declining measuring signals caused by excitation, then the relaxation time constant $T_2$ must be sufficiently large compared to the dwell time of the medium in the measuring section. The relaxation time constant $T_2$ is then sufficiently large compared to the dwell time when, in determining the flow velocity using the declining of the measuring signal based on the relaxation time constant $T_2$ for the respective implementation, the error is tolerable. Consequently, at a given relaxation time constant $T_2$, the determination of large flow velocities is more exact with a long measuring section than with a short measuring section. Thus, in a particularly preferred design of the nuclear magnetic flowmeter according to the invention, it is provided that the measuring sections of at least two of the antennae differ in length. Furthermore, the measurement results can be further improved when the lengths of the measuring sections of at least two of the antennae increase in the direction of flow of the medium.

The transmission of the excitation signals to the magnetized medium and the detection of the measuring signals is carried out by coil-like antennae. The transmission of the excitation signals to the magnetized medium can be conducted with a first coil and the detection of the measuring signals can be conducted with a second coil. In a further, particularly preferred design of the nuclear magnetic flowmeter according to the invention, on the other hand, it is provided that at least one of the antennae has a sole coil for transmitting the excitation signals to the magnetized medium and for detecting the signals. The design of the antennae with only a sole coil significantly reduces, on the one hand, the production efforts of the antennae, however, on the other hand, only slightly increases the efforts in the measuring unit.

The sole coil of one of the antennae having a sole coil can be a solenoid, wherein the magnetic field of the solenoid in the medium flowing in the measuring tube has at least one component parallel to the longitudinal axis of the measuring tube and the solenoid is arranged around the medium flowing in the measuring tube. The arrangement of the solenoid around the measuring tube means that the coil winding is implemented around the measuring tube. It is even possible to design the coil winding on the measuring tube so that the solenoid is a component of the measuring tube.

The antennae unit can have at least one antennae group, wherein the antennae group has at least two antennae each with a solenoid as sole coil and the measuring sections of the antennae having a solenoid as sole coil are consecutively arranged along the longitudinal axis of the measuring tube.

Two antennae are consecutively arranged when no further antenna is arranged between them.

It is advantageous when at least two of the consecutive measuring sections of at least one of the antennae groups are spaced by a measuring distance parallel to the longitudinal axis of the measuring tube for reducing the inductive coupling of the two consecutive antennae. Depending on the application, a certain amount of inductive coupling of two consecutive antennae is tolerable, wherein the tolerance level is a measure for the spacing of the two consecutive antennae.

In a further development of the design of the nuclear magnetic flowmeter according to the invention, it can be provided that at least two of the antennae spaced by one of the measuring distances of at least one of the antennae groups form a composite antenna with a composite measuring section, the composite measuring section consists of the measuring sections of the antennae and the measuring distance, and the composite antenna has the same properties over the composite measuring section as one of the two antennae over its respective measuring section. Accordingly, the antennae of one of the composite antennae can be operated separately with its respective measuring section, wherein the inductive coupling of the antennae is tolerable or is operated as composite antenna, wherein, over the composite measuring section, the composite antenna has the same properties as the antennae over the respective measuring sections.

In a further, particularly preferred design of the nuclear magnetic flowmeter according to the invention, it is provided that the antennae unit has at least one tapped coil having at least one tap. The tap separates the tapped coil into two coil sections and each of the coil sections forms one of the antennae. The antennae are, thus, not implemented as above by sole coils, but rather by a coil with taps, whereby production efforts are reduced.

The tapped coil can be a solenoid, wherein the magnetic field of the solenoid in the medium flowing in the measuring tube has at least one component parallel to the longitudinal axis of the measuring tube and the solenoid is arranged around the medium flowing in the measuring tube. The arrangement of the solenoid around the measuring tube means that the coil winding is implemented around the measuring tube. It is even possible to design the coil winding on the measuring tube so that the coils is a component of the measuring tube.

It has been seen to be advantageous for the quality of flow measurement when at least one of the antennae of at least one of the tapped coils has a compensation antenna for compensation of the magnetic field from the magnetic field generator effective in the medium outside of at least one of the measuring sections of the antennae formed by the tapped coil.

In another preferred design of the nuclear magnetic flowmeter according to the invention, it is provided that the sole coil of at least one of the antennae is a saddle coil and the magnetic field of the saddle coil in the medium flowing in the measuring tube has at least one component perpendicular to the longitudinal axis of the measuring tube.

While the solenoids have to be arranged around the measuring tube, the saddle coils are arranged on the side of the measuring tube or, as indicated by the name, are saddled on the measuring tube. Accordingly, the arrangement of saddle coils on the measuring tube is less of an effort than that of solenoids. A further, more important advantage of saddle coils as opposed to solenoids is the feature that the magnetic field is essentially perpendicular to the longitudinal axis of the measuring tube and does not extend parallel to it. This advantage is particularly useful when at least two of the saddle coils are arranged consecutively along the longitudinal axis of the measuring tube. The inductive coupling of two consecutively arranged saddle coils is much lower than that of two consecutively arranged solenoids.

A further development of the above described design of a nuclear magnetic flowmeter according to the invention provides that the antennae unit has at least one pair of antennae, the pair of antennae has two antennae each having a saddle coil as sole coil, the two antennae having a saddle coil as single coil are opposite one another in respect to the longitudinal axis of the measuring tube, the measuring sections of the two antennae are congruent, the direction of the magnetic field of the pair of antenna in the medium is described by an axis of the pair of antennae and the axis of the pair of antennae has at least one component perpendicular to the longitudinal axis of the measuring tube. The use of a pair of antennae consisting of two saddle coils instead of a sole saddle coil causes a stronger bundling of the magnetic field and a lower inductive coupling with neighboring antennae.

When the antennae unit has at least two pairs of antennae, the axes of the antennae pairs of both pairs of antennae can be oriented differently and the measuring section of the pairs of antennae can at least be overlapping. Different orientations of axes of antennae pairs causes reduced inductive coupling between the pairs of antennae.

In a preferred design of the nuclear magnetic flowmeter according to the invention, it is provided that at least one of the antennae is designed for generating a magnetic field, the magnetic field strength of the magnetic field has a gradient and the magnetic field in the medium extends at least over the measuring section of the at least one antennae. The gradient of the magnetic field strength can be such that the magnetic field strength increases linearly along an axis. The magnetic field can be generated by at least one permanent magnet and/or by at least one coil with current flowing through it. The same explanations that apply to the coils of the antennae apply to the design of the at least one coil.

The nuclear magnetic flowmeter according to the invention, in which the measuring sections of at least two of the antennae are different in length, can be operated using a method according to the invention, which is initially and essentially characterized in that excitation signals are generated by the measuring unit, that excitation signals are transmitted by the antenna to the flowing, magnetized medium located in the measuring section and the measuring signals excited by excitation signals in the medium from the medium located in the measuring section are detected by the antenna, that excitation signals are transmitted by the at least one further antenna to the flowing, magnetized medium located in the at least one further measuring section and the measuring signals excited by the excitation signals in the medium from the medium located in the at least one further measuring section are detected by the at least one further antenna, that derived measuring signals with at least reduced influence by dephasing are formed in that the measuring signals detected by the antenna and the measuring signals detected by the at least one further antenna are combined with one another, and that the velocity of the flowing medium is determined from the derived measuring signals.

Without limiting the invention, the method according to the invention is explained in detail in the following using the example of a nuclear magnetic flowmeter, whose antennae unit contains one antenna and only one further antenna, wherein the measuring section is arranged before the further measuring section in the direction of flow of the medium.

The antenna transmits an excitation signal at point $t_{0,1}$ to the medium located in the measuring section and the amplitude of the measuring signal $y_1$ at point $t_1$ detected by the antenna is $$\hat{y}_1(t_1) = y_{1,1}(t_1) y_{1,2}(t_1) \text{ with}$$

$$y_{1,1}(t_1) = 1 - \frac{v(t_1)}{l_1}(t_1 - t_{0,1}) \text{ and}$$

$$y_{1,2}(t_1) = \sum_{n=1}^{N} M_{1,n} F_n(t_1) e^{-\frac{t_1 - t_{0,1}}{T_{2,n}}}$$

The further antenna transmits an excitation signal at point $t_{0,2}$ to the medium located in the further measuring section and the amplitude of the measuring signal $y_2$ at point $t_2$ detected by the further antenna is $$\hat{y}_2(t_2) = y_{2,1}(t_2) y_{2,2}(t_2) \text{ with}$$

$$y_{2,1}(t_2) = 1 - \frac{v(t_2)}{l_2}(t_2 - t_{0,2}) \text{ and}$$

$$y_{2,2}(t_2) = \sum_{n=1}^{N} M_{2,n} F_n(t_2) e^{-\frac{t_2 - t_{0,2}}{T_{2,n}}}$$

For point $t_1$, $0 \le t_1 - t_{0,1} \le l_1/v$ has to be fulfilled and for point $t_2$, $0 \le t_2 - t_{0,2} \le l_2/v$ has to be fulfilled. $l_1$ is the length of the measuring section and $l_2$ is the length of the further measuring section, wherein $l_1 \ne l_2$. The index n identifies the individual phases of the medium containing N phases. In each phase, $M_{\{1,2\}}$ is the magnetization, F is the portion of the phase in the medium and $T_2$ is the already-mentioned relaxation time constant.

The first term $y_{\{1, 2\},1}$ in each case describes the declining of the amplitude $\hat{y}_{\{1, 2\}}$ of each measuring signal $y_{\{1, 2\}}$ due to the excited medium flowing out of the respective measuring section. The second term $y_{\{1, 2\},2}$ in each case describes the declining of the amplitude of the respective measuring signal by dephasing, which is described by the relaxation time constant $T_2$.

Determination of the flow velocity $v(t)$ at a point t with a sole antenna is known from the prior art. The determination requires the knowledge of the amplitude $\hat{y}_{\{1,2\}}(t)$ of the measuring signal, the length $l_{\{1, 2\}}$ of the measuring section, the magnetization $M_{\{1, 2\},n}$, the portion $F_n(t)$ of the phases in the medium and the relaxation time constant $T_{2,n}$.

According to the method according to the invention, the derived measuring signal is, for example, formed by combining the amplitude $\hat{y}_1(t_1)$ of the measuring signal detected by the antenna and the amplitude $\hat{y}_2(t_2)$ of the measuring signal detected by the further antenna.

The magnetization $M_{\{1, 2\},n}$ of the phases of the medium increases in the direction of flow of the medium over the magnetic field path until saturation magnetization. If the medium in the measuring section and in the further measuring section is not magnetized to saturation, a sufficiently equal magnetization of the medium in the measuring section and in the further measuring section can be set by a spacing distance with the length a parallel to the longitudinal axis of the measuring tube between the measuring section and the further measuring section. The spacing distance should be thereby measured such that the medium excited by the antenna reaches the further measuring section first when the medium excited by the further antenna has already completely flowed out of the measuring section, i.e. when the requirement $a \ge l_2$ is fulfilled. Otherwise, the medium excited by the antenna falsifies the measuring signal detected by the further antenna. Furthermore, the inductive coupling between the antenna and the further antenna should be sufficiently small. Taking the above explanations into consideration, the magnetizations are at least sufficiently the same in the second terms $y_{\{1, 2\},2}$, it is thus $M_{1,n} \approx M_{2,n}$.

The measuring points $t_{\{1, 2\}}$ in time can be chosen such that the change of the flow velocity is sufficiently low in the time interval between the measuring point $t_1$ and the measuring point $t_2$, thus $v(t_1) \approx v(t_2)$ and the change of the portions of the phases of the medium is sufficiently small, thus $F_n(t_1) \approx F_n(t_2)$.

Furthermore, the excitation points $t_{0,\{1, 2\}}$ in time are chosen so that at least $t_1 - t_{0,1} \approx t_2 - t_{0,2}$, whereby, taking the above explanations into consideration, the second terms $y_{\{1,2\},2}$ are overall sufficiently equal. The influence of the derived measuring signal by dephasing is, consequently, at least reduced. What is sufficient in the above explanations, is determined by the requirements of the respective application on the nuclear magnetic flowmeter.

The derived measuring signals can be quotients, wherein each of the quotients is formed from the measuring signal detected by an antenna and from the measuring signal detected by one of the remaining antenna and the measuring section of antenna and the measuring section of the other antenna differ in length. In terms of the example, the quotient is formed from the amplitude $\hat{y}_1(t_1)$ of the measuring signal detected by the antenna and the amplitude $\hat{y}_2(t_2)$ of the measuring signal detected by the further antenna:

$$\hat{y}'(t_1, t_2) = \frac{\hat{y}_1(t_1)}{\hat{y}_2(t_2)} \approx \frac{y_{1,1}(t_1)}{y_{2,1}(t_2)} = \frac{1 - \frac{v(t_1)}{l_1}(t_1 - t_{0,1})}{1 - \frac{v(t_2)}{l_2}(t_2 - t_{0,2})}$$

Preferably, the excitation signals are transmitted at the same time to the medium by the antenna and by at least one of the further antennae. Applied to the example, the excitation points $t_{0,\{1, 2\}}$ are chosen to be the same, whereby at least $t_1 \approx t_2$. Thereby, the derived measuring signal is $$\hat{y}'(t_1) = \frac{\hat{y}_1(t_1)}{\hat{y}_2(t_1)} = \frac{1 - \frac{v(t_1)}{l_1}(t_1 - t_{0,1})}{1 - \frac{v(t_1)}{l_2}(t_1 - t_{0,1})}$$

From this, the flow velocity can be calculated in a simple manner:

$$v(t_1) = \frac{l_1 l_2 (\hat{y}'(t_1) - 1)}{(\hat{y}'(t_1) l_1 - l_2)(t_1 - t_{0,1})}$$

For the determination according to the invention of the flow velocity of the medium in the measuring tube at an arbitrary point in time, only knowledge of the lengths of the measuring sections, the amplitudes of the measuring signals and of the excitation points in time are thereby required. Accordingly, the knowledge of the relaxation time constant $T_{2,n}$ is not required. Being able to determine the flow velocity of the medium without knowledge of the relaxation time constant $T_{2,n}$ can also be called self-calibration, since a calibration of the nuclear magnetic flowmeter with media having different known relaxation time constants $T_{2,n}$ is no longer necessary.

Since the flow velocity of the medium is now known, the effect of the flow velocity on the measuring signal detected by the antenna can be eliminated, resulting in the amplitude of a compensated measuring signal:

$$\hat{y}'_1(t_1) = \frac{\hat{y}_1(t_1)}{y_{1,1}(t_1)} = y_{1,2}(t_1) = \frac{\hat{y}_1(t_1)}{1 - \frac{v(t_1)}{l_1}(t_1 - t_{0,1})} = \sum_{n=1}^{N} M_{1,n} F_n(t_1) e^{\frac{-t_1 - t_{0,1}}{T_{2,n}}}$$

The amplitude of the compensated measuring signal, thus, corresponds to the amplitude of a measuring signal that results when the medium stands in the measuring tube. Consequently, relaxation time constants $T_{2,n}$ can be determined from the amplitudes of the compensated measuring signal. Then, using the relaxation time constants $T_{2,n}$, features correlated with the phases, such as the viscosities of the phases, can be determined.

In detail there is a plurality of possibilities for designing and further developing the nuclear magnetic flowmeter according to the invention as will be apparent from the following description of preferred embodiments in conjunction with the accompanying drawings.

DETAILED DESCRIPTION OF THE INVENTION

Figure 1:
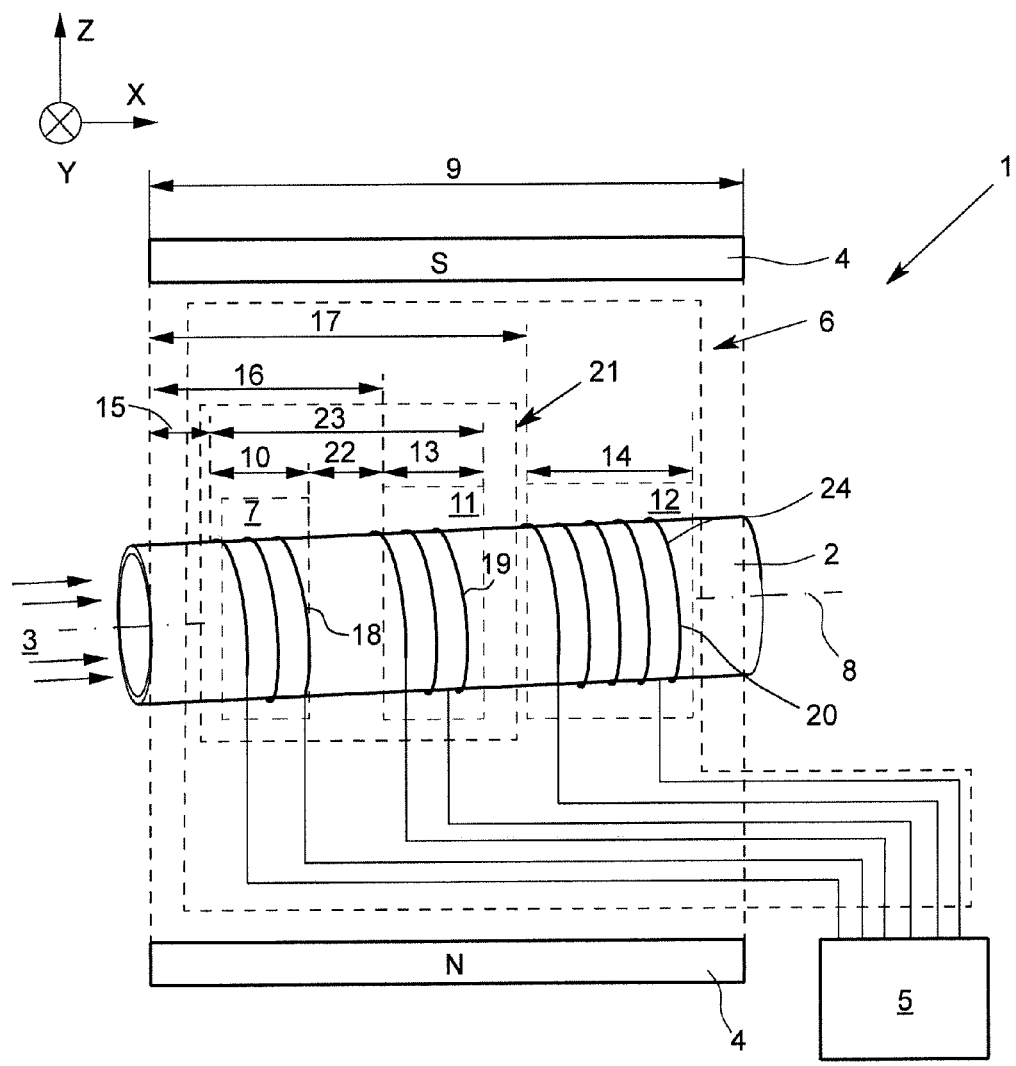
FIG. 1 is a first embodiment of a nuclear magnetic flowmeter according to the invention with three solenoids.

Elements of a first embodiment of a nuclear magnetic flowmeter 1 according to the invention are schematically shown in FIG. 1, which initially has one measuring tube 2 that has medium 3 flowing through it. The nuclear magnetic flowmeter 1 is designed for determining the flow of the medium 3 through the measuring tube 2, wherein the medium 3 can contain several phases. In order to determine the flow of the medium 3 through the measuring tube 2, the nuclear magnetic flowmeter 1 has a magnetic field generator 4, a measuring unit 5 and an antennae unit 6 with an antenna 7.

The longitudinal axis 8 of the measuring tube 2 is, by definition, aligned parallel to the x-axis of a Cartesian coordinate system, whereby the medium 3 flows parallel to the x-axis and, by definition, in the positive x-direction. The magnetic field generator 4 generates a magnetic field, which permeates the flowing medium 3, by definition, in the positive z-direction of the coordinate system, over a magnetic field path 9 aligned parallel to the x-axis. Thus, the direction of the flowing medium 3 and the direction of the magnetic field are oriented perpendicular to one another.

The measuring unit 5 is designed for generating excitation signals exciting the magnetized medium 3 and for measuring the measuring signals caused by the excitation signals in the magnetized medium 3.

The antenna 7 of the antennae unit 6 is designed for transmitting the excitation signals to the magnetized medium 3 and for detecting the measuring signals over a measuring section 10 aligned parallel to the x-axis and located in the magnetic field path 9. In addition to the antenna 7 with the measuring section 10, the nuclear magnetic flowmeter 1 according to the invention has a first further antenna 11 and a second further antenna 12. The first further antenna 11 is designed for transmitting the excitation signals to the magnetized medium 3 and for detecting the measuring signals over a first further measuring section 13 aligned parallel to the x-axis and located in the magnetic field path 9 and the second further antenna 12 is designed for transmitting the excitation signals to the magnetized medium 3 and for detecting the measuring signals over a second further measuring section 14.

The antennae unit 6 is designed for transmitting the excitation signals from the measuring unit 5 to the antenna 7, to the first further antenna 11 and to the second further antenna 12 and for transmitting the measuring signals from the antenna 7, from the first further antenna 11 and from the second further antenna 12 to the measuring unit 5.

The measuring unit 5 is designed for generation of and the antennae unit 6 for transmission of the excitation signals over any of the antennae 7, 11, 12, independent of the remaining antennae 7, 11, 12, to the magnetized medium 3, even simultaneously over more than one of the antennae 7, 11, 12. Furthermore, the measuring unit 5 is designed for measurement of and the antennae unit 6 for detection of the measuring signals of the excited medium 3 with any one of the antennae 7, 11, 12, independent of the remaining antennae 7, 11, 12 or also even simultaneously with more than one of the antennae 7, 11, 12. In particular, it is also possible to transmit an excitation signal to the medium 3 over one or several of the antennae 7, 11, 12 and to detect the measuring signal caused by the excitation signal in the medium 3 with one or several other of the antennae 7, 11, 12. Preferably, the antennae 7, 11, 12, with which a measuring signal is detected, are arranged along the x-axis in respect to the positive x-direction at the same level as or behind the antennae 7, 11, 12, via which the excitation signals causing the measuring signals are transmitted to the medium 3.

The length of the measuring section 10 of the antenna 7 is less than the length of the first further measuring section 13 of the first further antenna 11 and the length of the first further measuring section 13 is less than the length of the second further measuring section 14 of the second further antenna 12. Along the x-axis in respect to the positive x-direction, the first further antenna 11 is arranged behind the antenna 7 and the second further antenna 12 is arranged behind the first further antenna 11. Parallel to the x-axis, the medium 3 flowing in the measuring tube 2 covers a first inlet distance 15 from the beginning of the magnetic field path 9 to the beginning of the measuring section 10, a first further inlet distance 16 from the beginning of the magnetic field path 9 to the beginning of the first further measuring section 13 and a second further inlet distance 17 from the beginning of the magnetic field path 9 to the beginning of the second further measuring section 13. In respect to the arrangement of the antennae 7, 11, 12, the length of the inlet distance 15 is less than the length of the first further inlet distance 16 and the length of the first further inlet distance 16 is less than the length of the second further inlet distance 17. The lengths of the inlet distances 15, 16, 17 correspond to the respective exposure duration of the magnetic field generated by the magnetic field generator 4 on the flowing medium 3. In general, measuring sections are clearly defined by their length parallel to the x-axis and by their position on the x-axis. Thus, the measuring sections 10, 13, 14 are different.

The antenna 7 has a solenoid 18, the first further antenna 11 has a first further solenoid 19 and the second further antenna 12 has a second further solenoid 20 as sole coil for transmitting the excitation signals to the magnetized medium 3 and for detecting the measuring signal. The solenoids 18, 19, 20 are arranged around the measuring tube 2 such that the magnetic field of the solenoids 18, 19, 20 with current flowing through them have at least one component parallel to the x-axis in the flowing medium 3.

The medium 3 flowing through the measuring tube 2 is magnetized by the magnetic field of the magnetic field generator 4 active in the positive z-direction. Thereby, the atomic nuclei precess with a magnetic moment around the z-axis without phase relation to one another. An excitation signal generated by the measuring unit 5, whose frequency spectrum includes the Larmor frequency, is transmitted from the antennae unit 5 to at least one of the antennae 7, 11, 12. This excitation signal causes an alternating magnetic field with one component in the x-direction in the chosen solenoid 18, 19, 20, through which a torque is exerted on the precessing atomic nuclei of the medium 3, which turns the precessing atomic nuclei in the x-y-plane and causes the precessing of the atomic nuclei to be in-phase. The medium 3 excited in this manner induces a measuring signal in at least one of the solenoids 18, 19, 20, which is transmitted from the antennae unit 6 to the measuring unit 5.

The antenna 7 and the first further antenna 11 arranged behind the antenna 7 form an antennae group 21. The measuring section 10 of the antenna 7 and the first further measuring section 13 of the first further antenna 11 are spaced by a measuring distance 22 parallel to the x-axis in order to reduce inductive coupling of the solenoid 18 and the first further solenoid 19. In addition, the antennae group 21 forms a composite antenna with a composite measuring section 23. The composite measuring section 23 is made up of the measuring section 10 of the antenna 7, the measuring distance 22 and the first further measuring section 13. Over the composite measuring section 23, the composite antenna has the same characteristics in respect to the medium 3 as the antenna 7 over the measuring section 10 and the first further antenna 11 over the first further measuring section 13.

Figure 2:
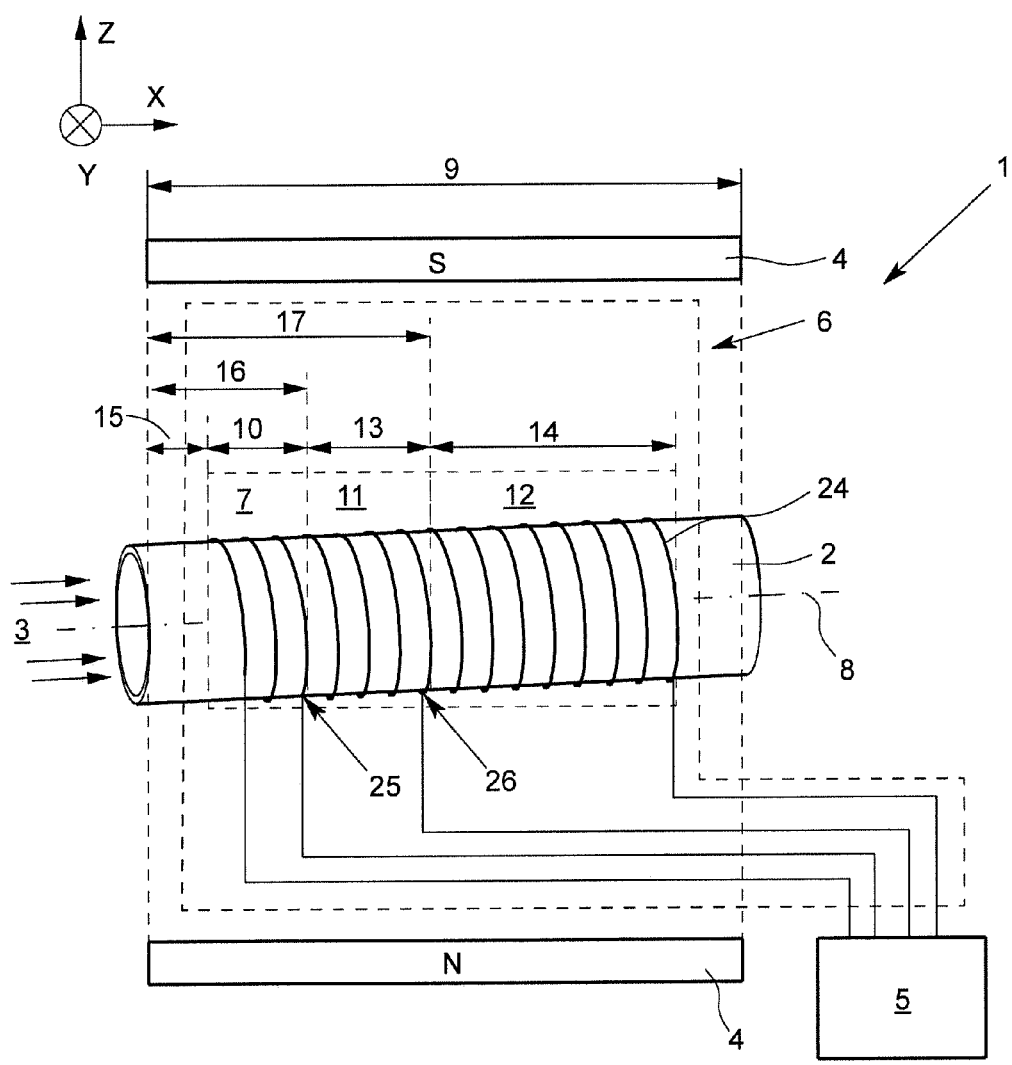
FIG. 2 is a second embodiment of a nuclear magnetic flowmeter according to the invention with a sole tapped solenoid.

Elements of a second embodiment of a nuclear magnetic flowmeter 1 according to the invention are schematically shown in FIG. 2. As opposed to the embodiment shown in FIG. 1, the antennae unit 6 contains only a sole coil 24 for transmitting the excitation signals to the magnetized medium 3 and for detecting the measuring signals. The sole coil 24 is a tapped coil designed as solenoid with a first tap 25 and a second tap 26. The tapped coil 24 is arranged around the medium 3 flowing the in the measuring tube 2 and the magnetic field has at least one component parallel to the x-axis in the medium 3 flowing in the measuring tube 2. The tap 25 and the tap 26 separate the tapped coil 24 into a first coil section, a second coil section and a third coil section. The first coil section forms the antenna 7 with the measuring section 10, the second coil section forms the first further antenna 11 with the first further measuring section 13 and the third coil section forms the second further antenna 12 with the second further measuring section 14. The remaining explanations for the first embodiment shown in FIG. 1 apply to the embodiment shown in FIG. 2.

Figure 3A:
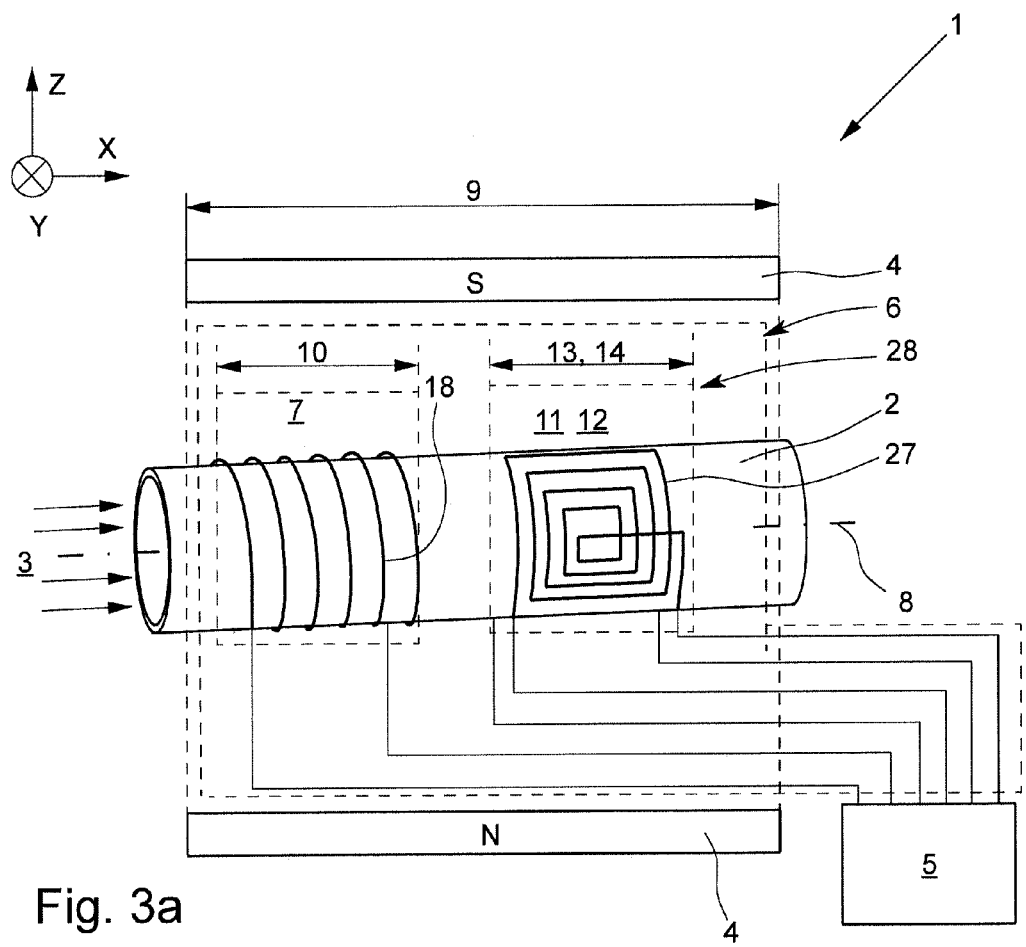
FIG. 3a, 3b is a third embodiment of a nuclear magnetic flowmeter according to the invention with a solenoid and two saddle coils.
Figure 3B:
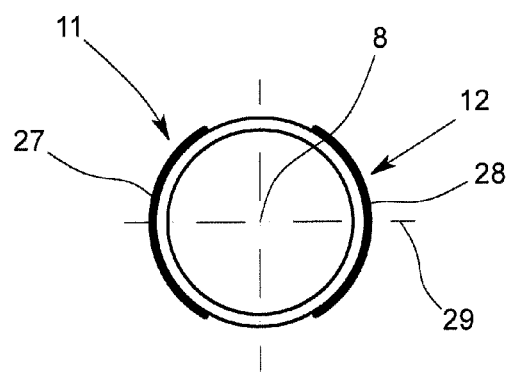

Elements of a third embodiment of a nuclear magnetic flowmeter 1 according to the invention are schematically shown in FIGS. 3a and 3b. In addition to the solenoid 18 forming the antenna 7 with the measuring section 10, the antenna unit 6 has a first saddle coil 27 and a second saddle coil 28. The first saddle coil 27 forms the first further antenna 11 over the first further measuring section 13 and the second further saddle coil 28 forms the second further antenna 12 over the second further measuring section 14.

The magnetic field of each of the saddle coils 27, 28 has at least one component parallel to the y-axis in the medium 3 flowing in the measuring tube 2. In contrast, the magnetic field of the solenoid 18 has at least one component parallel to the x-axis in the medium 3 flowing in the measuring tube 2. Due to the different directions of the magnetic fields of the solenoid 18, on the one hand, and the magnetic fields of the saddle coils 27, 28, on the other hand, the inductive coupling between the solenoid 18 and the saddle coils 27, 28 is less than if the saddle coils 27, 28 were replaced by a solenoid having at least one component parallel to the x-axis. The quality of the measured data is improved by the lower inductive coupling.

The first further antenna 11 and the second further antenna 12 are arranged opposite one another around the measuring tube 2 in respect to the x-axis, in such a manner that the first further measuring section 13 and the second further measuring section 14 are congruent. The direction of the common magnetic field of the first saddle coil 27 and the second saddle coil 28 in the flowing medium 3 is described by an axis 29 of the pair of antennae that coincides with the y-axis. The remaining explanations for the first embodiment shown in FIG. 1 also apply for this embodiment.

What is claimed is:

1. Nuclear magnetic flowmeter (1) for determining the flow of a medium flowing through a measuring tube (2) having a magnetic field generator (4), a measuring unit (5) and an antennae unit (6) with an antenna (7), wherein the magnetic field generator (4) permeates the flowing medium (3) with a magnetic field having at least a component perpendicular to a longitudinal axis (8) of the measuring tube over a magnetic field path (9) aligned parallel to the longitudinal axis (8) of the measuring tube for magnetizing the medium, wherein the measuring unit (5) is designed to generate excitation signals exciting the magnetized medium (3) and to measure measuring signals caused by the excitation signals in the magnetized medium (3), wherein the antenna (7) is designed as a coil and is designed for transmitting the excitation signals to the magnetized medium (3) and for detecting the measuring signal over a measuring section (10) aligned parallel to the longitudinal axis (8) of the measuring tube and located in the magnetic field path (9), and wherein the antennae unit (6) has at least one further antenna (11, 12), wherein the further antenna (11, 12) is designed as a coil and is designed for transmitting the excitation signals to the magnetized medium (3) and for detecting the measuring signals over a further measuring section (13, 14) aligned parallel to the longitudinal axis (8) of the measuring tube and located in the magnetic field path (9), and wherein the measuring section (10) and the further measuring section (13, 14) are different.

2. Nuclear magnetic flowmeter (1) according to claim 1, wherein winding densities of at least two of the antennae (7, 11, 12) designed as coils are the same.

3. Nuclear magnetic flowmeter (1) according to claim 1, wherein the measuring sections (10, 13, 14) of at least two of the antennae (7, 11, 12) have different lengths.

4. Nuclear magnetic flowmeter (1) according to claim 3, wherein the lengths of the measuring sections (10, 13, 14) of at least two of the antennae (7, 11, 12) increase in a direction of flow of the medium (3).

5. Nuclear magnetic flowmeter (1) according to claim 1, wherein at least one of the antennae (7, 11, 12) has a sole coil for transmitting the excitation signals to the magnetized medium (3) and for detecting the measuring signal.

6. Nuclear magnetic flowmeter (1) according to claim 5, wherein the sole coil of at least one of the antennae (7, 11, 12) having a single coil is a solenoid (18, 19, 20), the magnetic field of the solenoid (18, 19, 20) in the medium (3) flowing in the measuring tube (2) has at least one component parallel to the longitudinal axis (8) of the measuring tube and the solenoid (18, 19, 20) is arranged around the medium (3) flowing in the measuring tube (2).

7. Nuclear magnetic flowmeter (1) according to claim 6, wherein the antennae unit (6) has at least one antennae group (21), the antennae group (21) has at least two antennae (7, 11) each with a solenoid (18, 19) as sole coil and the measuring sections (10, 13) of the antennae (7, 11) having a solenoid (18, 19) as sole coil are consecutively arranged along the longitudinal axis (8) of the measuring tube.

8. Nuclear magnetic flowmeter (1) according to claim 7, wherein at least two of the consecutive measuring sections (10, 13) of at least one of the antennae groups (21) are spaced by a measuring distance (22) parallel to the longitudinal axis (8) of the measuring tube for reducing inductive coupling of the two consecutive antennae (7, 11).

9. Nuclear magnetic flowmeter (1) according to claim 8, wherein at least two of the antennae (7, 11) spaced by one of the measuring distances (22) of at least one of the antennae groups (21) form a composite antenna with a composite measuring section (23), the composite measuring section (23) consists of the measuring sections (10, 13) of the antennae (7, 11) and the measuring distance (22), and the composite antenna has the same properties over the composite measuring section (23) as one of the two antennae (7, 11) over its respective measuring section (10, 13).

10. Nuclear magnetic flowmeter (1) according to claim 1, wherein the antennae unit (6) has at least one tapped coil (24) having at least one tap (25, 26), the tap (25, 26) separates the tapped coil (24) into two coil sections and each of the coil sections forms one of the antennae (7, 11, 12).

11. Nuclear magnetic flowmeter (1) according to claim 10, wherein at least one of the tapped coils (24) is a solenoid, the magnetic field of the solenoid in the medium (3) flowing in the measuring tube (2) has at least one component parallel to the longitudinal axis (8) of the measuring tube and the solenoid is arranged around the medium (3) flowing in the measuring tube (2).

12. Nuclear magnetic flowmeter (1) according to claim 11, wherein at least one of the antennae (7, 11, 12) of at least one of the tapped coils (24) has a compensation antenna for compensation of the magnetic field from the magnetic field generator effective in the medium (3) outside of at least one of the measuring sections (10, 13, 14) of the antennae formed by the tapped coil (24).

13. Nuclear magnetic flowmeter (1) according to claim 5, wherein the sole coil of at least one of the antennae (11, 12) is a saddle coil (27, 28) and the magnetic field of the saddle coil (27, 28) in the medium (3) flowing in the measuring tube (2) has at least one component perpendicular to the longitudinal axis (8) of the measuring tube.

14. Nuclear magnetic flowmeter (1) according to claim 13, wherein the antennae unit (6) has at least one pair of antennae, the pair of antennae has two antennae (11, 12) each having a saddle coil (27, 28) as sole coil, the two antennae (11, 12) having a saddle coil (27, 28) as sole coil are opposite one another in respect to the longitudinal axis (8) of the measuring tube, the measuring sections (13, 14) of the two antennae (11, 12) are congruent, the direction of the magnetic field of the pair of antennae in the medium (3) is described by an axis (29) of the pair of antennae and the axis (29) of the pair of antennae has at least one component perpendicular to the longitudinal axis (8) of the measuring tube.

15. Nuclear magnetic flowmeter (1) according to claim 14, wherein the antennae unit (6) has at least two pairs of antennae, the axes of the antennae pairs (29) of the two pairs of antennae are oriented differently and the measuring sections (13, 14) of the pairs of antennae are at least overlapping.

16. Nuclear magnetic flowmeter (1) according to claim 1, wherein at least one of the antennae (7, 11, 12) is designed for generating a magnetic field, a magnetic field strength of the magnetic field has a gradient and the magnetic field in the medium extends over the measuring section (10, 13, 14) of the at least one antenna (7, 11, 12).

17. Method for operating a nuclear magnetic flowmeter (1) according to claim 1
wherein excitation signals are generated by the measuring unit (5),
wherein excitation signals are transmitted by the antenna (7) to the flowing, magnetized medium (3) located in the measuring section (10) and the measuring signals excited by excitation signals in the medium (3) from the medium (3) located in the measuring section (10) are detected by the antenna (7),
wherein excitation signals are transmitted by the at least one further antenna (11, 12) to the flowing, magnetized medium (3) located in the at least one further measuring section (13, 14) and the measuring signals excited by the excitation signals in the medium (3) from the medium (3) located in the at least one further measuring section (13, 14) are detected by the at least one further antenna (11, 12),
wherein derived measuring signals with at least reduced influence by dephasing are formed in that the measuring signals detected by the antenna (7) and the measuring signals detected by the at least one further antenna (11, 12) are combined with one another, and
that the velocity of the flowing medium (3) is determined from the derived measuring signals.

18. Method according to claim 17, wherein the derived measuring signals are quotients, wherein each of the quotients is formed from the measuring signal detected by one of the antennae (7, 11, 12) and from the measuring signal detected by another of the antennae (7, 11, 12) and wherein the measuring section (10, 13, 14) of the antenna and the measuring section (10, 13, 14) of the other antenna have different lengths.

19. Method according to claim 17 wherein the excitation signals are transmitted to the medium (3) by the antenna (7, 11, 12) and by at least one of the further antennae (7, 11, 12) at the same time.

* * * * *